(12) United States Patent
Knollenberg et al.

(10) Patent No.: US 10,197,487 B2
(45) Date of Patent: Feb. 5, 2019

(54) SYSTEMS AND METHODS FOR ISOLATING CONDENSATE IN A CONDENSATION PARTICLE COUNTER

(71) Applicant: PARTICLE MEASURING SYSTEMS, INC., Boulder, CO (US)

(72) Inventors: Brian Knollenberg, Boulder, CO (US); Stephen Pavone, Boulder, CO (US); Cliff Ketcham, Boulder, CO (US); Rebecca Thompson, Boulder, CO (US)

(73) Assignee: PARTICLE MEASURING SYSTEMS, INC., Boulder, CO (US)

( * ) Notice: Subject to any disclaimer, the term of this patent is extended or adjusted under 35 U.S.C. 154(b) by 0 days.

(21) Appl. No.: 15/611,497

(22) Filed: Jun. 1, 2017

(65) Prior Publication Data

US 2017/0350801 A1 Dec. 7, 2017

Related U.S. Application Data

(60) Provisional application No. 62/345,572, filed on Jun. 3, 2016.

(51) Int. Cl.
*G01N 1/00* (2006.01)
*G01N 15/06* (2006.01)
*G01N 15/00* (2006.01)
*G01N 15/14* (2006.01)

(52) U.S. Cl.
CPC ....... *G01N 15/065* (2013.01); *G01N 2015/03* (2013.01); *G01N 2015/1486* (2013.01)

(58) Field of Classification Search
CPC .. G01N 15/065; G01N 21/53; G01N 15/0205; B01D 47/05; G01F 1/661

USPC .......................................................... 356/37
See application file for complete search history.

(56) References Cited

U.S. PATENT DOCUMENTS

| | | | |
|---|---|---|---|
| 3,851,169 A | 11/1974 | Faxvog | |
| 4,348,111 A | 9/1982 | Goulas et al. | |
| 4,558,587 A * | 12/1985 | Fruzzetti | F16K 1/14 137/901 |
| 4,728,190 A | 3/1988 | Knollenberg | |
| 4,957,363 A | 9/1990 | Takeda et al. | |
| 5,085,500 A | 2/1992 | Blesener | |
| 5,107,883 A | 4/1992 | Shaw | |
| 5,121,988 A | 6/1992 | Blesener et al. | |
| 5,282,151 A | 1/1994 | Knollenberg | |
| 5,467,188 A | 11/1995 | Miyashita | |
| 5,642,193 A | 6/1997 | Girvin et al. | |

(Continued)

OTHER PUBLICATIONS

Grimm Aerosol Technik (2012) "Stationary Condensation Particle Counters (CPCs) Models 5.410-5.421," Accessible on the Internet at URL: http://wiki.grimm-aerosol.de/images/a/a0/D_e_cpc_stationary_2012_v1.pdf, 4 pgs. [Last Accessed Jan. 12, 2018].

(Continued)

*Primary Examiner* — Md M Rahman
(74) *Attorney, Agent, or Firm* — Leydig, Voit & Mayer, Ltd.

(57) ABSTRACT

The systems and methods provided herein relate generally to the prevention of migration of condensate in a condensation particle counter between components designed to handle condensate (e.g. saturator, condenser, condensate reservoir) and components which may be damaged by the condensate (e.g. detection and flow control devices).

17 Claims, 4 Drawing Sheets

(56) References Cited

U.S. PATENT DOCUMENTS

| | | | |
|---|---|---|---|
| 5,864,399 A | 1/1999 | Girvin et al. | |
| 5,920,388 A | 7/1999 | Sandberg et al. | |
| 5,946,092 A | 8/1999 | Defreez et al. | |
| 6,567,157 B1 * | 5/2003 | Flagan | G01N 1/2247 356/335 |
| 6,859,277 B2 | 2/2005 | Wagner et al. | |
| 7,030,980 B1 | 4/2006 | Sehler et al. | |
| 7,053,783 B2 | 5/2006 | Hamburger et al. | |
| 7,777,867 B2 | 8/2010 | Hopke et al. | |
| 8,030,080 B2 | 10/2011 | Spence et al. | |
| 8,465,791 B2 | 6/2013 | Liu et al. | |
| 9,175,781 B2 | 11/2015 | Reilley | |
| 2002/0134137 A1 | 9/2002 | Ondov et al. | |
| 2004/0012772 A1 * | 1/2004 | Ahn | G01N 15/065 356/37 |
| 2008/0148874 A1 * | 6/2008 | Wei | F02D 41/1466 73/865.5 |
| 2010/0280434 A1 * | 11/2010 | Raney | A61F 9/00745 604/22 |
| 2012/0131989 A1 * | 5/2012 | Vanhanen | G01N 15/06 73/28.01 |
| 2013/0032210 A1 | 2/2013 | Johnstone et al. | |
| 2014/0033915 A1 | 2/2014 | Hering et al. | |
| 2015/0000595 A1 | 1/2015 | Gorbunov et al. | |
| 2016/0201816 A1 * | 7/2016 | Rastegar | F16K 17/386 137/2 |
| 2016/0299047 A1 * | 10/2016 | Molla | B01L 3/502784 |

OTHER PUBLICATIONS

MSP Corporation (2011) "Product Information: Model 1110—WCPC," Accessible on the Internet at URL: https://development.mspcorp.com/resources/msp-1110-rev-c.pdf, 2 pgs. [Last Accessed Jan. 12, 2018].

Pinterich (May 2013) "The versatile Size Analyzing Nuclei Counter (vSANC)," European Aerosol Conference 2013, Prague, Czech Republic, 1 pg.

TSI Incorporated (2014) "Ultrafine Condensation Particle Counter Model 3776," Accessible on the Internet at URL: http://tsi.com/uploadedFiles/_Site_Root/Products/Literature/Spec_Sheets/3776_2980345.pdf, 4 pgs. [Last Accessed Jan. 12, 2018].

International Search Report with Written Opinion corresponding to Interantional Patent Application No. PCT/US2017/035499, dated Aug. 22, 2017.

* cited by examiner

SYSTEMS AND METHODS FOR ISOLATING CONDENSATE IN A CONDENSATION PARTICLE COUNTER

CROSS-REFERENCE TO RELATED APPLICATIONS

This application claims priority to and the benefit of U.S. Provisional Patent Application No. 62/345,572 filed Jun. 3, 2016, which is hereby incorporated by reference in its entirety to the extent not inconsistent herewith.

BACKGROUND OF INVENTION

This invention is in the field of condensation particle counters or condensation nuclei counters. In an embodiment, provided herein are systems and methods that prevent the migration of condensate from components of the system designed to contain condensate (e.g. condensate reservoir, saturator, or condenser) to components which may be damaged or interfered with by the presence of a condensate (e.g. particle counters, optical components of an optical particle counter, and flow control devices such as orifices).

A large portion of the micro-contamination industry and clean manufacturing industries is reliant on the use of particle counters, such as are described in a number of U.S. Patents, including U.S. Pat. Nos. 3,851,169, 4,348,111, 4,957,363, 5,085,500, 5,121,988, 5,467,188, 5,642,193, 5,864,399, 5,920,388, 5,946,092, and 7,053,783. Particle counters are also described in U.S. Pat. Nos. 4,728,190, 5,282,151, 6,859,277, and 7,030,980, which are hereby incorporated by reference in their entirety.

A conventional condensation particle counter allows for the detection of small particles using relatively low sensitivity particle counter devices, for example optical particle counters, by increasing detectability of the particle by condensing a vapor into a liquid on the particles' surface, increasing the apparent volume of the particle. The fluid being condensed on the particle is commonly referred to as the condensate or working fluid. Typically, a sample to be analyzed enters the condensation particle counter system through a flow control device (e.g. a flow orifice) and into a saturator where the sample is mixed with a concentration of condensate primarily in the vapor form. The saturator is in fluid communication with a condensate reservoir which provides condensate to the saturator, where it is heated to ensure it is sufficiently in the vapor phase. The sample stream, now mixed with condensate vapor, then flows into a condenser which cools the sample stream, causing the condensate to condense as a liquid around particles contained in the sample stream, thereby enlarging the perceived particle by creating a layer of liquid around the particle. The sample stream is then provided to a particle detection system, such as an optical particle counter, which more easily detects the particle due to the larger signature caused by the liquid layer.

Many different fluids are suitable as working fluids, but common examples include alcohols, water and glycerol. Depending on the particle detection device, the condensate may be harmful if allowed to interact with the sensitive components of the detection system or problematic if allowed to interfere with the small volumes of the flow control devices. Thus, problems can arise when the condensation particle counter system is moved, either within a laboratory or transported to a different destination, as the condensate may migrate away from the saturator and condenser components and into the optics or flow control devices. This problem is compounded if the system is not maintained in an upright position during transportation, as the saturator and condenser are often positioned to prevent condensate migration while the system is upright.

These problems are further magnified when a viscous and/or wettable condensate (e.g. glycerol) is used in the condensation particle counter system. While viscous and/or wettable condensates provide certain advantages in operation of the condensation particle counter, the higher viscosity and wettability increases the propensity of the working fluid to be retained in the device and, thus, available to migrate to different device components even after the device has been drained to remove condensate. This leads to condensate migration problems during shipping, even if the condensate reservoir has been drained and device is shipped or transported after the vast majority of the condensate has been removed.

It can be seen from the foregoing that there remains a need in the art for systems and methods which prevent the migration of condensate in a condensation particle counter to protect sensitive components.

SUMMARY OF THE INVENTION

The systems and methods provided herein relate generally to the prevention of migration of condensate in a condensation particle counter between components designed to handle condensate (e.g. saturator, condenser, condensate reservoir) and components which may be damaged by the condensate (e.g. detection and flow control devices). In some embodiments, the systems and methods automatically engage to protect the sensitive components when the condensation particle counter is not in use, when condensation particle counter has no power, or when the pump for flowing a sample through the particle counter is not running. The systems and methods are versatile and may be used with different counting systems, for example, optical particle counters (including scattered, emission and transmission counters). Advantageously, in some embodiments, the described systems and methods allow for the shipping or transport of a condensation particle counter with the condensate in situ, removing the need to drain and replace the condensate for transportation.

In an aspect, provided is a condensation particle counter system comprising: (i) an inlet for introducing a sample stream to be analyzed; (ii) a saturator for introducing a condensate into the sample stream; wherein the saturator is in fluid communication with a condensate reservoir; (iii) a condenser in fluid communication with the saturator for condensing the condensate onto particles contained in the sample stream; (iv) a particle counter in fluid communication with the condenser for detecting or characterizing the particles in the sample stream; and a valve positioned between the particle counter and the condenser for isolating the particle counter from the condenser, the saturator and the condensate reservoir. In an embodiment, the condensation particle counter system further comprises: a second valve positioned between the inlet and the saturator for isolating the inlet from the condenser, the saturator and the condensate reservoir.

In an embodiment, for example, the valve is configured to automatically close when no power is supplied to the particle counter or a vacuum pump, thereby isolating the particle counter. In an embodiment, the valve is configured to automatically close when there is no sample fluid flow through the inlet or when there is a change in an ambient temperature. In embodiments, the valve and the second valve are configured to automatically close when no power is supplied to the particle counter or a vacuum pump, thereby isolating the particle counter and the inlet. In embodiments, for example, the condensation particle counter is a scattered light particle counter, an emitted light particle counter or a transmission particle counter. In an embodiment, the valve and/or the second valve is a pinch valve.

In an embodiment, the condensation particle counter system further comprises, a flow control orifice positioned between the inlet and the saturator, wherein the second valve is positioned between the flow control orifice and the saturator and further isolates the flow control orifice from the condenser, the saturator and the condensate reservoir. In embodiments, for example, the condensate is water, methanol, ethanol, propanol, butanol, glycerol, or a combination thereof. In an embodiment, for example, the condensate is glycerol.

In an aspect, provided is a method for isolating condensate in a condensation particle counter comprising: (i) providing a condensation particle counter comprising: (a) an inlet with a flow control orifice; (b) a saturator for introducing condensate in fluid communication with a condensate reservoir; (c) a condenser for condensing the condensate onto particles; (d) an particle counter for detecting and characterizing the particles; and (ii) isolating the saturator, the condenser and the condensate reservoir from the inlet and the particle counter, thereby preventing condensate from contaminating the particle counter or the flow control orifice. In an embodiment, the step of isolating the saturator, the condenser and the particle counter is performed by a first valve positioned between the saturator and the inlet and a second valve positioned between the condenser and the particle counter.

In embodiments, for example, the first valve and the second valve are pinch valves. In embodiments, the step of isolating is performed when the particle counter is not operational, when the particle counter is powered off, and/or there is no flow through the flow orifice. In an embodiment, the particle counter is an optical particle counter.

In an aspect, provided is a condensation particle counter system comprising: (i) an inlet with a flow control orifice for introducing a sample stream to be analyzed; (ii) a saturator for introducing a condensate into the sample stream; wherein the saturator is in fluid communication with a condensate reservoir; (iii) a condenser in fluid communication with the saturator for condensing the condensate onto particles contained in the sample stream; (iv) a particle counter in fluid communication with the condenser for detecting or characterizing the particles in the sample stream; (v) a first valve positioned between the particle counter and the condenser for isolating the particle counter from the condenser, the saturator and the condensate reservoir; a second valve positioned between the inlet and the saturator for isolating the flow control orifice from the condenser, the saturator and the condensate reservoir; wherein the first valve and the second valve are configured to automatically close when the particle counter is not operational, the particle counter is powered off and/or there is no flow through the flow orifice.

DETAILED DESCRIPTION OF THE INVENTION

Figure 1:
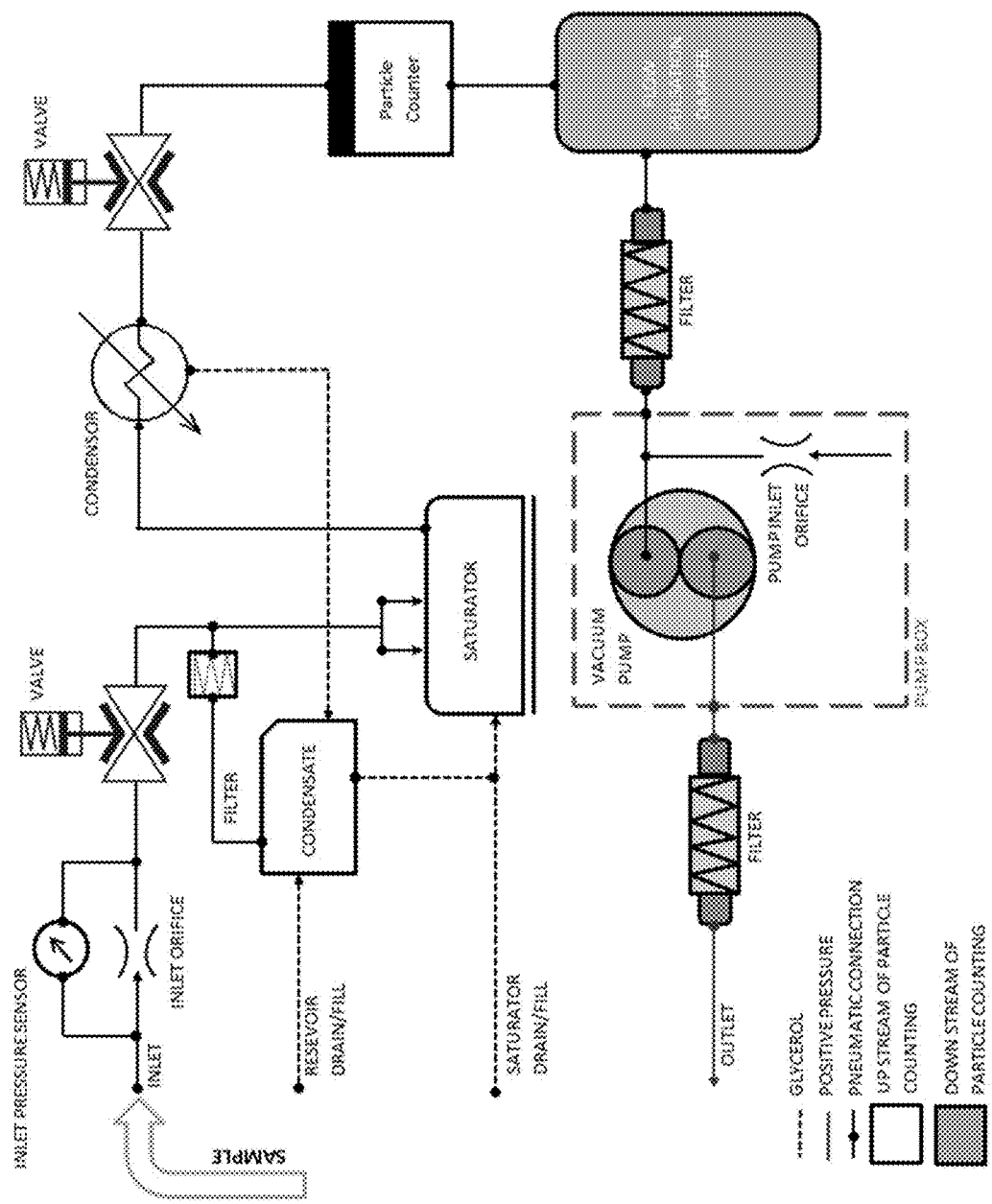
FIG. 1. Provides a schematic an embodiment of the invention which uses pinch valves to isolate a condensate (e.g. glycerol).
Figure 2:
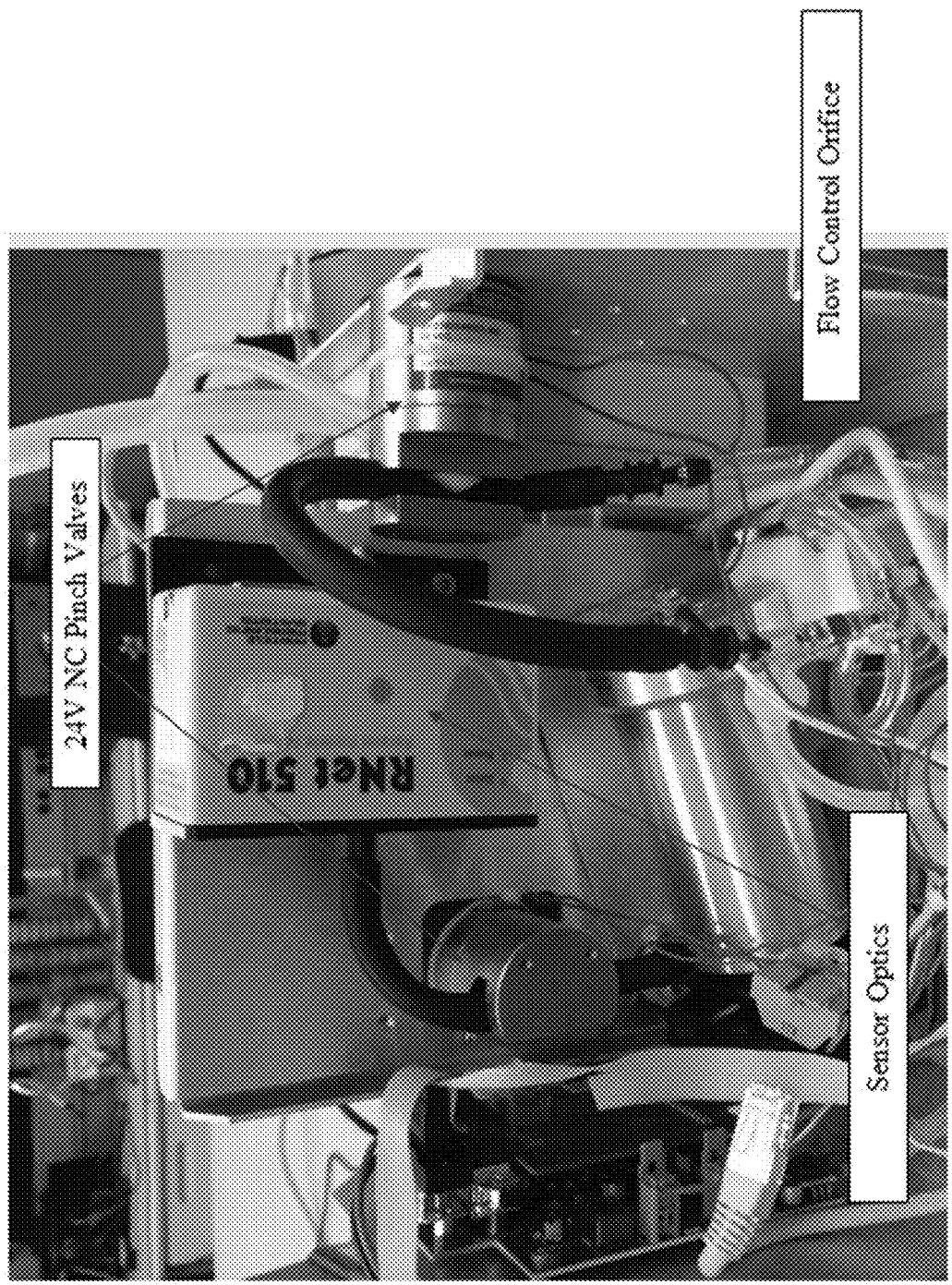
FIG. 2. Provides a photograph of the embodiment described in FIG. 1.
Figure 3:
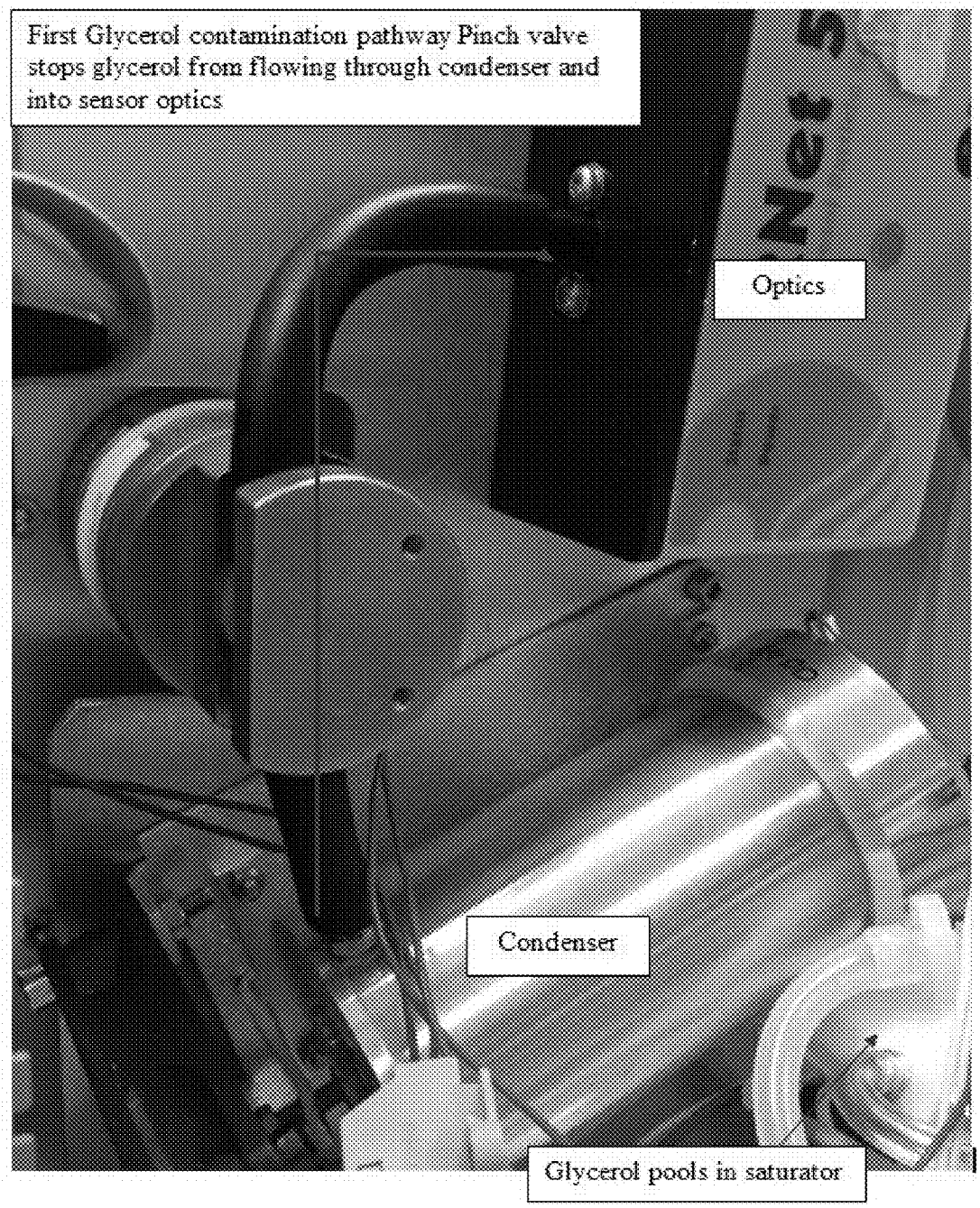
FIG. 3. Provides a photograph of the valve which isolates the particle counter in the embodiment of FIG. 1.
Figure 4:
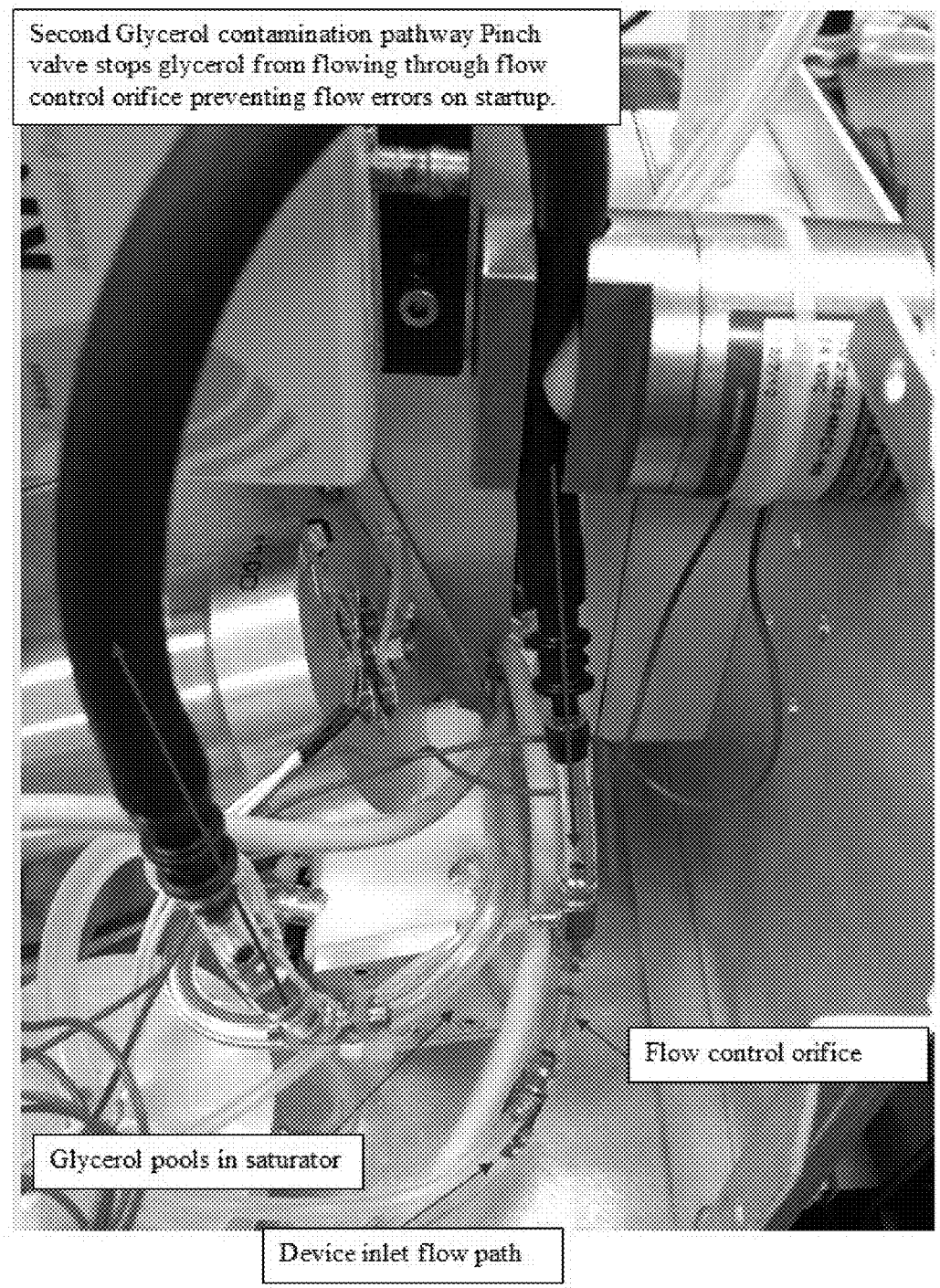
FIG. 4. Provides a photograph of the valve which isolates the sample inlet and inlet orifice in the embodiment of FIG. 1.

In general the terms and phrases used herein have their art-recognized meaning, which can be found by reference to standard texts, journal references and contexts known to those skilled in the art. The following definitions are provided to clarify their specific use in the context of the invention.

"Flow direction" and "sample flow" are used synonymously herein and refer to an axis parallel to the direction the bulk of a fluid is moving when a fluid is flowing. For fluid flowing through a straight flow cell, the flow direction is parallel to the path the bulk of the fluid takes. For fluid flowing through a curved flow cell, the flow direction may be considered tangential to the path the bulk of the fluid takes.

"Condensation particle counter" and "condensation nuclei counter" are used synonymously herein and refer to systems or devices with a particle counter (as defined herein) and a condensation system for enlarging the perceived volume of particles by the particle counter by condensing a condensate on the surface of the particles. In some embodiments, the particle counter and condensation system are combined into a single system or unit and in some cases they comprise two or more units or devices. In an embodiment, for example, the particle counter is an optical particle counter and is included with a condensation system in a single device.

"Condensate" and "working fluid" are used synonymously herein and refer to the fluid condensed by the condensation particle counter on to the particle in order facilitate detection by the particle counter. In some embodiments, condensate refers to an alcohol, water or glycerol. In an embodiment, for example, condensate refers to glycerol.

The expression "detecting a particle" broadly refers to sensing, identifying the presence of and/or characterizing a particle. In some embodiments, detecting a particle refers to counting particles. In some embodiments, detecting a particle refers to characterizing and/or measuring a physical characteristic of a particle, such as diameter, cross sectional dimension, shape, size, aerodynamic size, or any combination of these.

"Particles" refers to small objects which are often regarded as contaminants. A particle can be any material created by the act of friction, for example when two surfaces come into mechanical contact and there is mechanical movement. Particles can be composed of aggregates of material, such as dust, dirt, smoke, ash, water, soot, metal, minerals, or any combination of these or other materials or contaminants. "Particles" may also refer to biological particles, for example, viruses, spores and microorganisms including bacteria, fungi, archaea, protists, other single cell microorganisms and specifically those microorganisms having a size on the order of 1-15 µm. A particle may refer to any small object which absorbs or scatters light and is thus detectable by an optical particle counter. As used herein, "particle" is intended to be exclusive of the individual atoms or molecules of a carrier fluid, for example water molecules, process chemical molecules, oxygen molecules, helium atoms, nitrogen molecules, etc. Some embodiments of the present invention are capable of detecting, sizing, and/or counting particles comprising aggregates of material having a size greater than 10 nm, 20 nm, 30 nm, 50 nm, 100 nm, 500 nm, 1 µm or greater, or 10 µm or greater. In some embodiments, the instrumentation is capable of detecting particles having a size selected from 20 nm to 50 nm, 50 nm to 50 µm, a size selected from 100 nm to 10 µm, or a size selected from 500 nm to 5 µm.

The term "particle counter" refers to systems capable of detecting particles suspended in a fluid, systems capable of determining the sizes of particles suspended in a fluid, systems capable of counting particles suspended in a fluid, systems capable of classification of particles suspended in a fluid, or any combination of these. In some embodiments, particle counter refers to an optical particle counter comprised of several components, such as a source for generating a beam of electromagnetic radiation, optics for directing the beam into a region where a fluid sample is flowing, for example a liquid or gas flowing through a flow cell. A typical optical liquid particle counter is also comprised of a photodetector, such as a two-dimensional optical detector, and collection optics for detecting electromagnetic radiation which is obscured, scattered or emitted by particles which pass through the beam, and other electronics for the processing and analysis of electrical signals produced by the photodetector including current to voltage converters and signal filtering and amplification electronics.

"Fluid communication" refers to the arrangement of two or more objects such that a fluid can be transported to, past, through or from one object to another. For example, in some embodiments two objects are in fluid communication with one another if a fluid flow path is provided directly between the two objects. In some embodiments, two objects are in fluid communication with one another if a fluid flow path is provided indirectly between the two objects, such as by including one or more other objects or flow paths between the two objects. In one embodiment, two objects present in a body of fluid are not necessarily in fluid communication with one another unless fluid from the first object is drawn to, past and/or through the second object, such as along a flow path.

"Isolation" or "Isolating" refer to limiting or eliminating fluid communication between two or more components, for example, by closing a valve.

"Flow rate" refers to an amount of fluid flowing past a specified point or through a specified area, such as through a detection zone of a liquid particle counter. In one embodiment a flow rate refers to a mass flow rate, i.e., a mass of the fluid flowing past a specified point or through a specified area. In one embodiment a flow rate is a volumetric flow rate, i.e., a volume of the fluid flowing past a specified point or through a specified area.

The invention is further detailed in the following Examples, which are offered by way of illustration and are not intended to limit the scope of the invention in any manner.

Example 1—Automatic Isolation of Condensate Tied to System Power

In an embodiment, the condensation isolation system is configured to automatically engage the isolation systems when the power of the condensation particle counter is off and is described in FIG. 1. Connecting the means of condensate isolation directly to the device power avoids user errors, in some embodiments, automatic shutting of the valves can occur when the vacuum pump is not providing suction or when the device is not in operation. Once power is connected to the device and the power switch is turned on the isolation valves open and allow the sample to flow through the system. FIG. 1 illustrates pinch valves, but embodiments may employ any valve type such as ball valves, check valves, needle valves, diaphragm valves or popper valves. A passive system where the default condition closes the isolation valve(s) will ensure that anytime the device is shipped or transported a significant distance the valves are closed and condensate is isolated. The system also provides other benefits by isolating the condensate from the external environment, for example, the condensate tends to be volatile and may be lost as a vapor if not isolated. Further, the isolation also prevents other vapors, chemicals, or particulates from entering the condensate when not in use, protecting the purity of the working fluid.

After the startup procedure, warm-up and decision to begin sampling, a sample will be drawn into the device at the inlet. Immediately upon entering the device the sample will pass through an orifice whose function is to create a difference in the flow stream pressure, reading this pressure the device can adjust pump speed to create the desired flow rate (e.g. 2.8 L/min). This orifice is the first component to be protected by the valves. Because condensate is stored in both the saturator and condensate fill reservoir, it can, during shipping, rough handling or movement, pass through the open pneumatic pathways of the device and either occlude the orifice rendering the flow calibration inaccurate or become aerosolized at the inlet and cause false counts for the device.

Next, the sample stream passes through the first valve and enters the saturator. The first valve may be positioned anywhere in the device upstream from the saturator. In the saturator, condensate is vaporized and the flow stream will entrain this vaporized condensate while flowing towards the condenser. The condenser cools the sample to promote condensation of the condensate. The condenser temperature will specific to the condensate being used by the system and example systems contain 21 mL of total condensate within the system. At the condenser the condensate condenses onto any particles by in the sample stream, thereby enlarging them for later sensing by the particle counter. The vast majority of the vaporized condensate condenses on the walls and pools in the bottom of the condenser. This is significant because the condensate may readily flow once condensed on the sides of the condenser (especially in cases of viscous and/or wettable condensates such as glycerol) and becomes difficult to remove from the device before shipping or relocation.

The flow stream next exits the condenser and flows through the second valve, in some embodiments, a pinch valve. The second valve may be positioned anywhere in the device between the condenser and particle counter. This valve is designed to stop the flow of condensate to the particle counter and its integral and expensive sensing components. Without the described condensate isolation system, condensate from both the saturator and recycled condensate from the condenser would have clear pathways during shipping or rough handling towards the particle counter.

The particle counter characterizes particles in the sample stream, for example, counting or determining the size of the particles. Different types of particle counters may be implemented relying on different interactions with the particle to characterize it. An example would be an optical particle counter which provides a beam of electromagnetic radiation into a flow chamber containing the sample. An optical collection system collects light scattered or emitted by the particles as they pass through the flow chamber and a detection system provides an electric signal based on the light collected, thereby characterizing the particles.

After sensing at the particle counter, the flow enters a pulsation dampener used to dampen pump pulsations and then through a filter which protects the pump from any particulate in the airstream. The pump then sends the sample through a second filter to clean any particles from the pump itself and then out to the device outlet. The pump inlet orifice on the vacuum side of the pump simply draws a vacuum on the pump box to keep any particles migrating from the pump out of the device interior and external environment.

STATEMENTS REGARDING INCORPORATION BY REFERENCE AND VARIATIONS

All references throughout this application, for example patent documents including issued or granted patents or equivalents; patent application publications; and non-patent literature documents or other source material; are hereby incorporated by reference herein in their entireties, as though individually incorporated by reference, to the extent each reference is at least partially not inconsistent with the disclosure in this application (for example, a reference that is partially inconsistent is incorporated by reference except for the partially inconsistent portion of the reference).

The terms and expressions which have been employed herein are used as terms of description and not of limitation, and there is no intention in the use of such terms and expressions of excluding any equivalents of the features shown and described or portions thereof, but it is recognized that various modifications are possible within the scope of the invention claimed. Thus, it should be understood that although the present invention has been specifically disclosed by preferred embodiments, exemplary embodiments and optional features, modification and variation of the concepts herein disclosed may be resorted to by those skilled in the art, and that such modifications and variations are considered to be within the scope of this invention as defined by the appended claims. The specific embodiments provided herein are examples of useful embodiments of the present invention and it will be apparent to one skilled in the art that the present invention may be carried out using a large number of variations of the devices, device components and methods steps set forth in the present description. As will be obvious to one of skill in the art, methods and devices useful for the present methods can include a large number of optional composition and processing elements and steps.

When a group of substituents is disclosed herein, it is understood that all individual members of that group and all subgroups, are disclosed separately. When a Markush group or other grouping is used herein, all individual members of the group and all combinations and subcombinations possible of the group are intended to be individually included in the disclosure.

It must be noted that as used herein and in the appended claims, the singular forms "a", "an", and "the" include plural reference unless the context clearly dictates otherwise. Thus, for example, reference to "a cell" includes a plurality of such cells and equivalents thereof known to those skilled in the art, and so forth. As well, the terms "a" (or "an"), "one or more" and "at least one" can be used interchangeably herein. It is also to be noted that the terms "comprising", "including", and "having" can be used interchangeably. The expression "of any of claims XX-YY" (wherein XX and YY refer to claim numbers) is intended to provide a multiple dependent claim in the alternative form, and in some embodiments is interchangeable with the expression "as in any one of claims XX-YY."

Whenever a range is given in the specification, for example, a temperature range, a time range, or a composition or concentration range, all intermediate ranges and subranges, as well as all individual values included in the ranges given are intended to be included in the disclosure. It will be understood that any subranges or individual values in a range or subrange that are included in the description herein can be excluded from the claims herein.

All patents and publications mentioned in the specification are indicative of the levels of skill of those skilled in the art to which the invention pertains. References cited herein are incorporated by reference herein in their entirety to indicate the state of the art as of their publication or filing date and it is intended that this information can be employed herein, if needed, to exclude specific embodiments that are in the prior art. For example, when compositions of matter are claimed, it should be understood that compounds known and available in the art prior to Applicant's invention, including compounds for which an enabling disclosure is provided in the references cited herein, are not intended to be included in the composition of matter claims herein.

As used herein, "comprising" is synonymous with "including," "containing," or "characterized by," and is inclusive or open-ended and does not exclude additional, unrecited elements or method steps. As used herein, "consisting of" excludes any element, step, or ingredient not specified in the claim element. As used herein, "consisting essentially of" does not exclude materials or steps that do not materially affect the basic and novel characteristics of the claim. In each instance herein any of the terms "comprising", "consisting essentially of" and "consisting of" may be replaced with either of the other two terms. The invention illustratively described herein suitably may be practiced in the absence of any element or elements, limitation or limitations which is not specifically disclosed herein.

One of ordinary skill in the art will appreciate that starting materials, biological materials, reagents, synthetic methods, purification methods, analytical methods, assay methods, and biological methods other than those specifically exemplified can be employed in the practice of the invention without resort to undue experimentation. All art-known functional equivalents, of any such materials and methods are intended to be included in this invention. The terms and expressions which have been employed are used as terms of description and not of limitation, and there is no intention in the use of such terms and expressions of excluding any equivalents of the features shown and described or portions thereof, but it is recognized that various modifications are possible within the scope of the invention claimed. Thus, it should be understood that although the present invention has been specifically disclosed by preferred embodiments and optional features, modification and variation of the concepts herein disclosed may be resorted to by those skilled in the art, and that such modifications and variations are considered to be within the scope of this invention as defined by the appended claims.

We claim:
1. A condensation particle counter system comprising:
   an inlet for introducing a sample stream to be analyzed;
   a saturator for introducing a condensate into said sample stream; wherein said saturator is in fluid communication with a condensate reservoir;

a condenser in fluid communication with said saturator for condensing said condensate onto particles contained in said sample stream;
a particle counter in fluid communication with said condenser for detecting or characterizing said particles in said sample stream; and
a valve positioned between said particle counter and said condenser for isolating said particle counter from said condenser, said saturator and said condensate reservoir.

2. The condensation particle counter system of claim 1 further comprising:
a second valve positioned between said inlet and said saturator for isolating said inlet from said condenser, said saturator and said condensate reservoir.

3. The condensation particle counter system of claim 2, wherein said valve and said second valve are configured to automatically close when no power is supplied to said particle counter or a vacuum pump, thereby isolating said particle counter and said inlet.

4. The condensation particle counter system of claim 2, wherein said valve and said second valve are pinch valves.

5. The condensation particle counter system of claim 2 further comprising a flow control orifice positioned between said inlet and said saturator, wherein said second valve is positioned between said flow control orifice and said saturator and further isolates said flow control orifice from said condenser, said saturator and said condensate reservoir.

6. The condensation particle counter system of claim 1, wherein said valve is configured to automatically close when no power is supplied to said particle counter or a vacuum pump, thereby isolating said particle counter.

7. The condensation particle counter system of claim 1, wherein said valve is configured to automatically close when there is no sample fluid flow through said inlet.

8. The condensation particle counter system of claim 1, wherein said valve is configured to automatically close when there is a change in an ambient temperature.

9. The condensation particle counter system of claim 1, wherein said condensation particle counter is a scattered light particle counter, an emitted light particle counter or a transmission particle counter.

10. The condensation particle counter system of claim 1, wherein said valve is a pinch valve.

11. The condensation particle counter system of claim 1, wherein said condensate is water, methanol, ethanol, propanol, butanol, glycerol or a combination thereof.

12. The condensation particle counter system of claim 11, wherein said condensate is glycerol.

13. A method for isolating condensate in a condensation particle counter comprising:
providing a condensation particle counter comprising:
an inlet with a flow control orifice;
a saturator for introducing condensate in fluid communication with a condensate reservoir;
a condenser for condensing said condensate onto particles;
an particle counter for detecting and characterizing said particles; and
isolating said saturator, said condenser and said condensate reservoir from said inlet and said particle counter, thereby preventing condensate from contaminating said particle counter or said flow control orifice;
wherein said step of isolating said saturator, said condenser and said particle counter is performed by a first valve positioned between said saturator and said inlet and a second valve positioned between said condenser and said particle counter.

14. The method of claim 13, wherein said first valve and said second valve are pinch valves.

15. The method of claim 13, wherein said step of isolating is performed when the particle counter is not operational, when the particle counter is powered off, and/or there is no flow through said flow orifice.

16. The method of claim 13, wherein said particle counter is an optical particle counter.

17. A condensation particle counter system comprising:
an inlet with a flow control orifice for introducing a sample stream to be analyzed;
a saturator for introducing a condensate into said sample stream; wherein said saturator is in fluid communication with a condensate reservoir;
a condenser in fluid communication with said saturator for condensing said condensate onto particles contained in said sample stream;
a particle counter in fluid communication with said condenser for detecting or characterizing said particles in said sample stream;
a first valve positioned between said particle counter and said condenser for isolating said particle counter from said condenser, said saturator and said condensate reservoir; and
a second valve positioned between said inlet and said saturator for isolating said flow control orifice from said condenser, said saturator and said condensate reservoir;
wherein said first valve and said second valve are configured to automatically close when said particle counter is not operational, said particle counter is powered off and/or there is no flow through said flow orifice.

* * * * *